Figure 1:
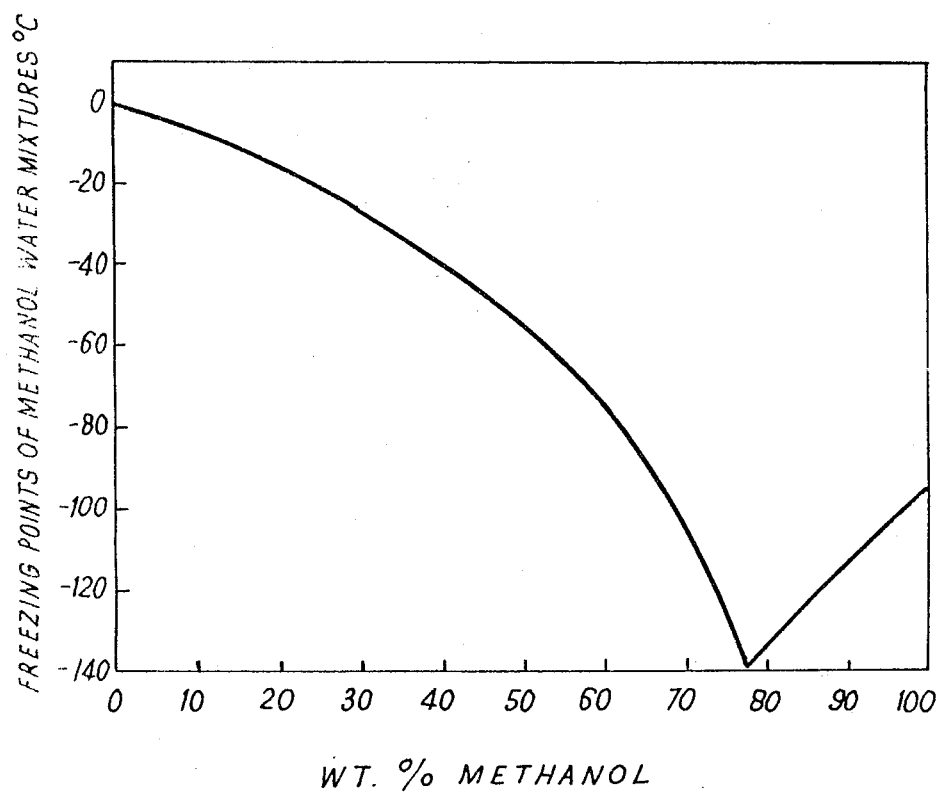

United States Patent [19]

Cummings et al.

[11] 4,406,774

[45] Sep. 27, 1983

[54] DEHYDRATION OF HYDROCARBONS

[75] Inventors: Donald R. Cummings, Cheltenham; Colin W. Braathen, Borehamwood, both of England

[73] Assignee: Dut Pty Limited, Sydney, Australia

[21] Appl. No.: 225,517

[22] Filed: Jan. 16, 1981

Related U.S. Application Data

[63] Continuation of Ser. No. 54,418, Jul. 3, 1979, abandoned.

[30] Foreign Application Priority Data

Jul. 17, 1978 [GB] United Kingdom ............... 30086/78

[51] Int. Cl.$^3$ ....................... C10G 33/04; C10G 21/00
[52] U.S. Cl. .................................... 208/130; 208/188; 62/17
[58] Field of Search ................. 208/188, 130; 210/41; 62/17; 55/68

[56] References Cited

U.S. PATENT DOCUMENTS

| | | | |
|---|---|---|---|
| 3,349,024 | 10/1967 | Mayhue | 208/130 |
| 3,761,538 | 9/1973 | Espino et al. | 208/130 X |
| 3,839,485 | 10/1972 | Wrisberg et al. | 208/130 |
| 3,925,047 | 12/1975 | Harper | 208/188 |
| 3,977,203 | 8/1976 | Hinton et al. | 62/17 |
| 4,002,558 | 1/1977 | Feldman | 208/188 |

*Primary Examiner*—Delbert E. Gantz
*Assistant Examiner*—Glenn Caldarola
*Attorney, Agent, or Firm*—Browdy and Neimark

[57] ABSTRACT

The tendency toward ice or solid hydrate formation during cooling of a light hydrocarbon or hydrocarbon mixture such as LPG or NGL for storage or transport at sub-zero temperatures is eliminated by mixing it with aqueous methanol solution in a mixer 5, cooling the mixture in cooler 8 and thereafter separating the hydrocarbon and aqueous phase in a separator 10, the solution being chosen to be substantially insoluble in the hydrocarbon phase and freeze below the temperature to which the mixture is cooled, and at least part of the aqueous phase being recycled by pump 17 to the mixer 5 for re-use with methanol being added as required to restore its concentration in the recycling liquor towards that of the initial aqueous solution and some of the recycling liquor being removed as required to restore the quantity of circulating liquor towards its initial level.

18 Claims, 3 Drawing Figures

DEHYDRATION OF HYDROCARBONS

This is a continuation of application Ser. No. 054,418, filed July 3, 1979, now abandoned.

This invention relates to dehydration of hydrocarbons, and especially to the suppression of the formation of ice and/or solid hydrates during cooling of light hydrocarbons containing water.

Light hydrocarbons (which term includes herein mixtures of hydrocarbons) are normally stored and transported in the liquid phase. Examples of light hydrocarbons are liquefied petroleum gas (LPG) consisting of propane or butane or an admixture of propane and butane with typically less than 10 mole percent of other hydrocarbons as impurities, and natural gas liquids (NGL) consisting chiefly of propane and butane but with substantial amounts (typically 10–40 mole percent) of impurities such as methane, ethane, pentane, hexane and heavier hydrocarbons. The term NGL as used herein also includes liquids with a high concentration of ethane together with appreciable concentrations of propane, butane and heavier components. Other examples of light hydrocarbons include gasoline and aviation turbine fuel (avtur).

LPG and NGL may be kept in the liquid state either by holding them at ambient temperature and high pressure, or, as is normally done in LPG carriers, at low temperature and ambient pressure.

However, in the latter case, the cooling of the hydrocarbon is accompanied by the undesirable formation of ice and solid hydrates unless steps are taken to remove any water present. Such dehydration is generally effected before the hydrocarbon material is loaded in to the LPG carrier.

The dehydration is normally effected in the gaseous state at moderate temperatures, using glycol which is regenerated, or in the liquid state using solid-dessicant absorbers. Both methods require relatively heavy, bulky equipment, and must have a heat source such as steam, high-pressure hot water or hot flue gases, for regeneration of the glycol or solid dessicant. In applications where space and utility supplies are limited, therefore, it may be desirable to employ other means of ice/hydrate suppression.

Methanol is well known as an ice/hydrate suppressant, having the advantages that methanol/water mixtures (a) can remain fluid at very low temperatures where glycol/water mixtures would be viscous, slushy or even solid, and (b) form a separate phase from the hydrocarbon phase thus offering a simple separation process.

However, methanol is not favoured over glycol as a drying agent for continuous use and regeneration. This is because methanol has a high vapour pressure compared with glycol, so that losses in the treated gas are substantial. Also, methanol has a lower boiling point than water, so that in the recovery of the methanol from the methanol/water mixture enough heat must be supplied to evaporate all the methanol dessicant, while in the case of glycol only enough heat need be supplied to evaporate the absorbed water which will be a relatively much smaller volume. Further, methanol is miscible with liquid light hydrocarbons when little or no water is present, so that if liquid-liquid contacting with substantially pure methanol is used, careful control must be maintained over the methanol flow rate to ensure that on the one hand enough methanol is used to ensure adequate ice/hydrate suppression, while on the other hand an excess is not used which would cause methanol loss as an impurity in the treated hydrocarbon. Such careful control over the methanol flow rate implies an accurate means of determining the suspended and dissolved water content of the liquid hydrocarbon feed stream, which is a very difficult measurement problem.

Despite the above disadvantages, methanol has found use in the clearing of lines and valves blocked by ice and hydrates, and a supply is routinely kept on hand in shore installations and on LPG carriers. The methanol is normally used as a once-through basis, and discarded after use.

The use of gasoline/methanol blends as fuel for internal combustion engines has been proposed, but the presence of dissolved and/or suspended water in gasoline as normally distributed from refineries can cause separation of a methanol/water-rich phase, particularly at low temperatures. This can be avoided by dehydration of the gasoline prior to methanol addition but present dehydration methods are not suitable for use on small quantities of liquids such as would have to be processed in roadside gasoline dispensing stations.

A similar problem exists with aviation gasoline on turbine fuel. These materials are routinely treated to remove suspended water, e.g. by means of coalescer devices, prior to fuelling the aircraft. However, at high altitudes and correspondingly low temperatures, a large proportion of the dissolved water (which is not removed by such devices) may separate as ice, giving the possibility of blockages in the fuel system.

The present invention provides a method of employing methanol to dehydrate, and especially reduce ice and hydrate formation in, light hydrocarbons which reduces or avoids the problems referred to above.

The method comprises removing water dissolved or dispersed in a light hydrocarbon (which term includes a mixture of hydrocarbons) by intimately mixing said hydrocarbon with a polar organic solvent which is very soluble in water, cooling the mixture whereby the water dissolved or dispersed in the hydrocarbon is absorbed preferentially in said solvent and a hydrocarbon phase and a solvent-containing aqueous phase are formed, and separating said phases, and wherein the solvent comprises methanol which is employed in the form of an aqueous solution thereof which is substantially insoluble in the hydrocarbon and has a freezing point below the temperature to which the mixture is cooled, and at least a part of the aqueous phase separated from the hydrocarbon phase after cooling is recycled to be mixed with fresh light hydrocarbon, and the methanol concentration of the liquor being recycled is continuously or intermittently restored towards that of the aqueous solution initially employed and the inventory of the liquor being recyled is continuously or intermittently restored towards its initial level.

The process will normally be carried out with the light hydrocarbon in liquid form and for the light hydrocarbon mixtures for which the process is particularly appropriate, e.g. LPG and NGL, it will generally be necessary to operate the process at superatmospheric pressure, e.g. up to about 300 psig.

In general, it is preferred to choose the aqueous methanol solution to have a freezing point at least 5° C., and more preferably from 5° C. to 15° C., below the temperature to which the mixture is cooled.

The invention also provides an apparatus for the dehydration of light hydrocarbons, the apparatus comprising a mixer for intimately mixing a light hydrocarbon with an aqueous methanol solution, and including an inlet for the light hydrocarbon, an inlet for aqueous methanol solution and an outlet for the mixture; means for cooling the mixture below ambient temperature; means for separating the cooled mixture into a dehydrated hydrocarbon phase and an aqueous phase; means for recirculating at least a part of the separated aqueous phase to the aqueous methanol solution inlet of the mixer for intimately mixing with more light hydrocarbon; means for intermittently or continuously withdrawing a portion of the recirculating aqueous phase and means for intermittently or continuously adding methanol to the recirculating aqueous phase.

Suitably the apparatus may include a coalescer for the mixture located between the cooling means and the separating means.

Suitably the mixer and the recirculating means may comprise an ejector.

The geographical location of the demand for the valuable olefin gases which can be obtained from light hydrocarbon mixtures such as LPG and NGL by steam cracking often makes it necessary for the steam cracking to be carried out at a location which is geographically remote from the point of supply of the light hydrocarbon and for the transfer of the light hydrocarbon to be effected at least in part by transportation on a tanker ship at sub-ambient temperature.

Two valuable sources of light hydrocarbon are natural gas and gas associated with naturally occurring oil (associated gas). The present invention permits the formation from these sources of light hydrocarbon mixtures suitable for storage and transport at sub-ambient temperatures and subsequent steam cracking, without the need for the complex facilities for removing water normally required at the point of supply and using equipment which is compact and relatively unaffected by tilting and which therefore can even be installed on a floating platform or barge, on a tower loading buoy or, in particular, on the tanker ship in which the light hydrocarbon is transported.

The light hydrocarbon steam is conveniently derived from the natural or associated gas simply by chilling a compressed stream thereof to produce a condensate the major portion of which is selected from $C_2$ to $C_4$ hydrocarbon and mixtures thereof.

Thus, in one preferred embodiment, the apparatus is installed on board a tanker ship and includes means for conveying dehydrated hydrocarbon from the separating means to the cargo space of the ship.

In another preferred embodiment of the apparatus, suitable for the treatment of gasoline or aviation fuel, the apparatus also includes a storage tank for the light hydrocarbon and a dispenser for dispensing the dehydrated hydrocarbon into the fuel tank of a vehicle which may be an automobile or an aircraft, first conduit means connecting the storage tank to the hydrocarbon inlet of the mixer and a second conduit for conveying dehydrated hydrocarbon from the separator to the dispenser.

By using a methanol/water solution as the treatment liquor, it is possible, by suitable choice of the treatment liquor circulation rate, to ensure that the hydrocarbon being reacted is in contact with a substantial excess of methanol over that required to ensure hydrate and ice suppression without excessive losses of methanol in the treated hydrocarbon product because in the presence of water the solubility of the methanol in the hydrocarbon is substantially reduced.

Thus, by means of the invention it is possible to use a treatment liquor which can cope with large surges in the water content of the hydrocarbon with only minimal loss of methanol to the hydrocarbon phase and it is therefore not necessary to measure accurately the water content of the hydrocarbon. All that is required is the relatively simple matter of monitoring the concentration of methanol in a methanol/water solution.

The concentration of methanol in the aqueous methanol solution admixed with the hydrocarbon depends on the amount of the solution which is mixed with the hydrocarbon and the expected maximum amount of water associated with (i.e. dissolved or dispersed in) the hydrocarbon stream and must be such that the aqueous phase which is separated from the hydrocarbon phase after cooling the mixture, and which comprises the original solution plus water which has been absorbed from the hydrocarbon phase, does not freeze at the separation temperature. The minimum methanol content of the aqueous phase for a given temperature can be determined from the phase diagram shown in FIG. 1 of the accompanying drawings. Decrease in the amount of solution mixed with the hydrocarbon or increase in the expected maximum water content of the hydrocarbon increases the required methanol concentration in the initial solution and vice versa. Decreasing the temperature at which the separation occurs increases the amount of the methanol required and vice versa.

It is preferred that the quantity of the solution that is mixed with the hydrocarbon is such that the water content of the aqueous phase after cooling does not exceed that of the initial solution by 20%, and more preferably by 5%, by weight.

In general the methanol concentration of the initial solution will be in the range 20 to 60% by weight although higher or lower concentrations may be used. The amount of solution mixed with the hydrocarbon will normally be 5 to 50% by weight of the hydrocarbon although higher or lower amounts may be used. For example, where it is expected that the hydrocarbon may contain slugs of entrained water, the amount may exceed 100%.

The combination of the required maximum water content in the hydrocarbon after treatment together with the equilibria between the hydrocarbon and water/methanol mixtures and the efficiency of the separation of the hydrocarbon from the aqueous phase, both of which can be readily determined using known principles, determines the temperature to which the mixture of hydrocarbon and aqueous methanol solution is cooled. In general, it will be in the range 0° to −60° C. and usually in the range −20° C, to −60° C.

The mixing of the hydrocarbon and the aqueous methanol solution can be effected in any suitable manner which achieves intimate mixing e.g. in any mixer known in the art for this purpose. The cooling may be effected in any manner suitable for a two phase dispersion. After cooling, the aqueous phase, comprising the aqueous methanol solution diluted with water which was originally associated with the light hydrocarbon, may be separated from the dehydrated hydrocarbon phase in any suitable manner, e.g. by settling, if desired with the aid of a coalescer.

Because of the uptake of water from the hydrocarbon into the aqueous methanol solution to form the aqueous phase that is separated from the hydrocarbon after cooling, as the treatment proceeds the inventory of the aqueous stream that is being recycled will increase and the methanol concentration will decrease, and it is necessary to take steps to restore the inventory of the aqueous stream towards its original level and the methanol concentration towards that of the aqueous methanol solution initially employed. This may be achieved continuously or intermittently. The control of the inventory may suitably be effected, for example, by including a tank in the recycle circuit equipped with a liquid level sensor controlling e.g. a discharge or simple overflow. The methanol concentration may be controlled by sensing a property of the recycling stream, which is related in simple manner to the methanol concentration, e.g. density, and adding fresh methanol to the recycling stream either continuously or intermittently as required. Control of the inventory and the methanol can be effected automatically, if desired.

The process of the invention is particularly suitable for treating a light hydrocarbon e.g. LPG or NGL, as it is being loaded on board a tanker ship for transport. It can be operated using simple, compact and unsophisticated equipment which is particularly adapted to be installed in a confined space such as on an offshore oil production platform or on board the tanker itself. When the process is used for this purpose, the control of the inventory and methanol content of the recycling stream will generally be continuous and automatic.

The process is also suitable for the treatment of gasoline or aviation fuel e.g. at a roadside gas station or on an airfield. In the former case, the control of the inventory and methanol content of the recycling stream may conveniently be intermittent and non-automated; in the latter case, however, control will generally be continuous and automatic.

The process is particularly suitable for treating gasoline to which dry methanol is to be added as a gasoline extender. Amounts up to 25% of dry methanol, depending on the nature of the gasoline, may be added to the dehydrated gasoline.

Figure 2:
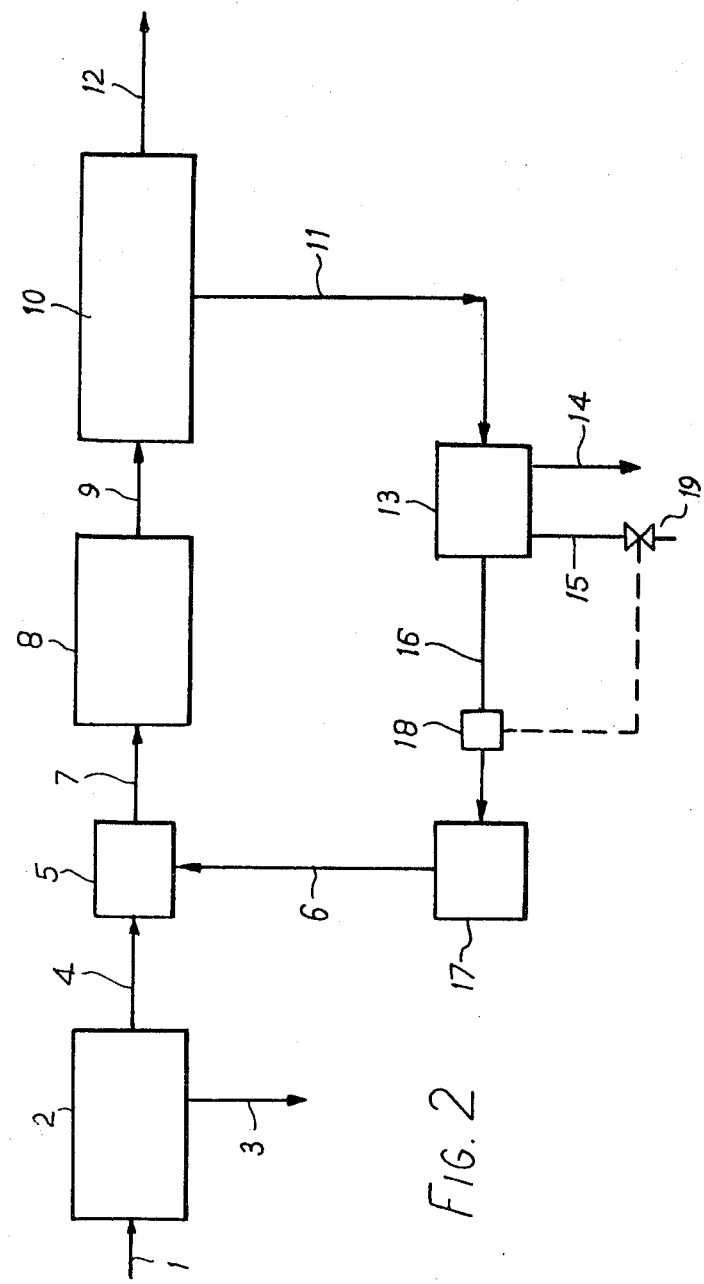
Figure 3:
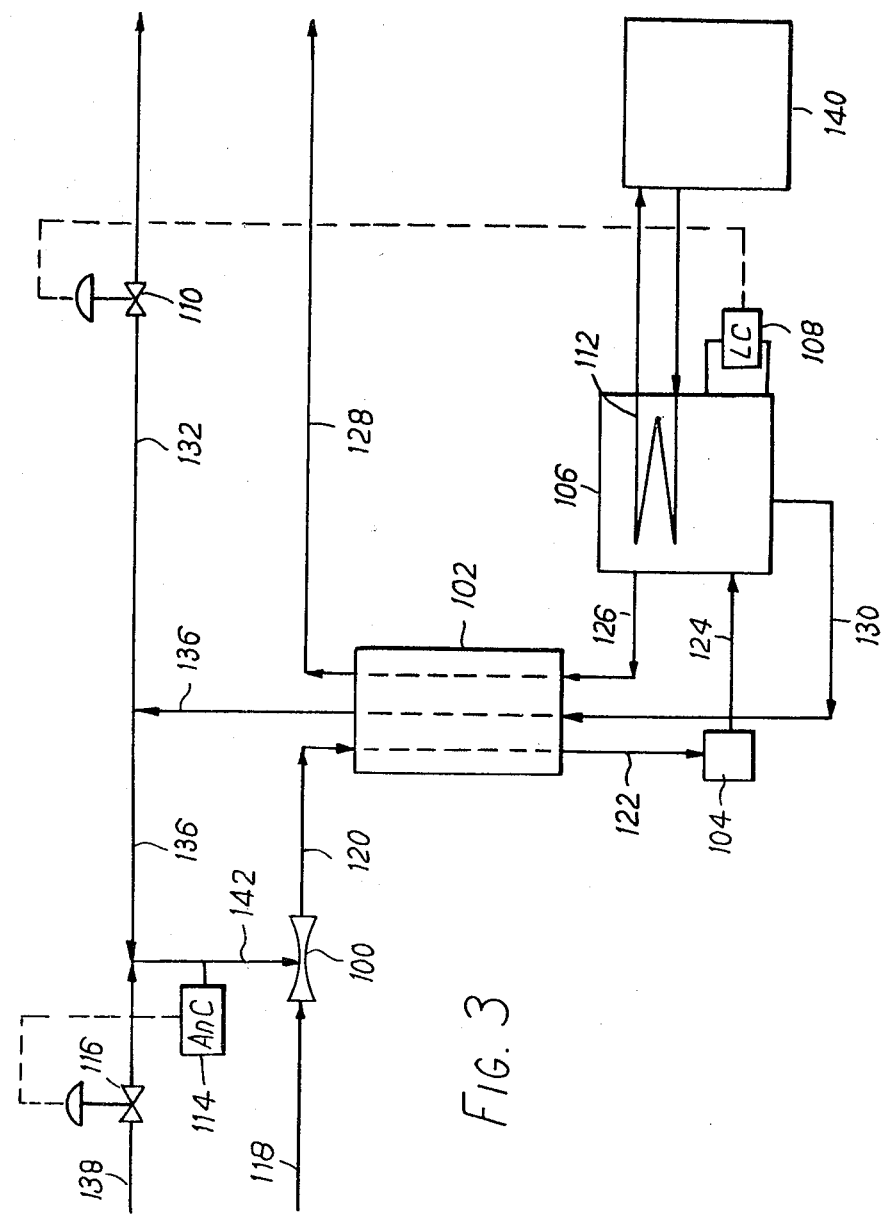

The invention is now described with reference to two embodiments thereof and with the aid of the accompanying drawings in which FIG. 2 is a flow diagram of an embodiment suitable for treating a light hydrocarbon which is to be transported in a tanker ship while stored below ambient temperature, and FIG. 3 is a flow diagram of an embodiment suitable for treating gasoline, e.g. for subsequent blending with methanol, or for treating an aviation fuel.

Referring to FIG. 2, 2 represents a primary separator, 5 is a mixing means, 8 is a cooler, 10 is a secondary separator and 17 is a pump.

Pressurised hydrocarbon liquid e.g. LPG, at ambient temperature and containing dissolved and suspended water, passes via feed pipeline 1 to primary separator 2. A substantial proportion of the suspended water is separated in separator 2 and flows to disposal via pipeline 3. The pressurised hydrocarbon liquid, now substantially denuded of suspended water, but still containing dissolved water, passes via pipeline 4 to mixing means 5 where it is mixed with an aqueous methanol solution entering via pipeline 6. The proportions of water and methanol in said solution are such that its freezing point is sufficiently below the intended final temperature to which the hydrocarbon liquid is to be cooled that it is capable of absorbing the maximum amount of water expected to be contained in the hydrocarbon liquid and that it is substantially insoluble in the hydrocarbon liquid.

From mixing means 5, the suspension of aqueous methanol solution in said hydrocarbon liquid passes via pipeline 7 to cooler 8, where it is cooled to the desired temperature which is low enough to ensure that said hydrocarbon liquid can be stored or transported at atmospheric pressure. From cooler 8, the cooled suspension passes via pipeline 9 to secondary separator 10, where the aqueous phase comprising the initial aqueous methanol solution, now enriched in water by virtue of the absorption of suspended and dissolved water from the hydrocarbon liquid, is separated and removed via pipeline 11. The dehydrated hydrocarbon liquid, now at a safe storage temperature, passes from separator 10 via pipeline 12, e.g. to storage in the cargo tanks of a ship. The aqueous phase in pipeline 11 is passed to purge/make-up device 13, where excess is removed in pipeline 14, and sufficient make-up methanol is subsequently added via pipeline 15, to counter the effects of dilution by the water removed from said hydrocarbon liquid so that the methanol concentration in the aqueous methanol solution in pipeline 16 by which the solution leaves purge make-up device 13 and the inventory of the recycling stream are maintained substantially constant. The removal of excess aqueous phase in pipeline 14 may be accomplished for example by means of a simple overflow pipe from a tank in which the solution is collected.

Automatic control of the supply of make-up methanol through pipeline 15 is effected in the illustrated embodiment by analysis of the methanol/water solution in pipeline 16 by analyser 18, the signal from analyser 18 being employed to control the rate of flow of methanol through pipeline 15, e.g. by a valve 19; the arrangement being such that if the sensed concentration of methanol varies from a predetermined value, the signal so obtained acts to adjust valve 19 to change the rate of flow of the methanol in pipeline 15 to restore the concentration of methanol in pipeline 16 towards the predetermined value. As indicated above, the analyser may alternatively be located to analyse the solution in pipeline 11.

The analysis of the methanol/water solution may be accomplished by any of several known means, for example density determination, refractive index determination, bubble point determination or other means.

The methanol/water solution passes from line 16 to pump means 17, whence it is returned at a controlled rate to mixing means 5 via pipeline 6.

While the apparatus described above may be installed on land or on an oil production platform off-shore, it is particularly suitable for installation in the tanker ship into which the hydrocarbon is being loaded.

Referring now to FIG. 3, the hydrocarbon liquid (gasoline or aviation turbine fuel) is supplied from bulk storage via a pump (not shown) in pipeline 118, where it is mixed with recirculating methanol/water treatment solution in ejector 100. It will be appreciated that use of ejector 100 is not vital to the application of the invention, but is merely a convenient way of ensuring intimate mixing of the hydrocarbon liquid and treatment solution, fixing the relative quantities of hydrocarbon liquid and treatment solution to be mixed, and also providing motive power for the recirculation of the treatment solution. Flow control instrumentation and a pump could be used as an alternative to the ejector. From ejector 100 the two-phase mixture of hydrocarbon liquid and treatment solution passes via pipeline 120 to heat exchanger 102, where it is passed in indirect countercurrent heat exchange to treated hydrocarbon liquid and recirculating treatment solution and is cooled whereby to dehydrate the hydrocarbon, the water being absorbed in the methanol/water mixture. From exchanger 102 the two-phase mixture, now chilled, passes to a coalescer device 104, where the droplet size of the dispersed phase is increased to enhance separation. The two-phase mixture of hydrocarbon liquid and aqueous phase then passes from coalescer 104 via pipeline 124 to separation and buffer vessel 106 where it separates into an upper layer of hydrocarbon liquid, and a lower aqueous phase. The upper layer is drawn off via pipeline 126 to pass through heat exchanger 102 and pipeline 128 to a suitable dispensing means, or to short-term buffer storage. The lower, aqueous, layer is drawn from buffer vessel 106 via pipeline 130 to pass to heat exchanger 102. The level of treatment solution in buffer vessel 106 is maintained by interface level controller 108 acting on control valve 110. Cooling coil 112 in buffer vessel 106 controls the minimum temperature achieved in the treatment process, and provides the necessary temperature differential at the cold end of exchanger 102. Refrigerant for cooling coil 112 is supplied by a conventional refrigeration unit 140.

From exchanger 102 the recirculating treatment solution passes via pipeline 136 to ejector 100, after removal of a water-rich draw-off stream via pipeline 132 and valve 110, and addition of a pure methanol, or methanol-rich, stream via pipeline 138 and control valve 116. The rate of draw-off via pipeline 132 depends on the interface level in vessel 106 which varies with the amount of water removed from the hydrocarbon. The rate of introduction of fresh methanol in line 138 is controlled by analysis controller 114 which may, for example, sense the density of the aqueous liquid in pipeline 142 and operate the valve 116 to control the flow in pipeline 138 to maintain the methanol concentration in pipeline 142 substantially constant.

Where the hydrocarbon is gasoline, the apparatus may include means for adding dried methanol to the dehydrated gasoline prior to providing it to the means for dispensing it into a vehicle's fuel tank.

The invention is further illustrated by the following Examples.

EXAMPLE 1

112,000 lb/hr of LPG supplied at about 300 psig and a temperature in the range 10° to 35° C. and containing 2.5% by weight of dissolved and suspended water is simultaneously dehydrated and cooled to −50° C. using the process and apparatus described with reference to FIG. 2 of the drawings e.g. in the process of being pumped into a cargo space of a tanker ship for storage in the cooled state for transport. The compositions and flow rates of the various streams are set out below.

| Pipeline No | Flow lbs/hr | Composition wt % | | |
|---|---|---|---|---|
| | | Hydrocarbon | Methanol | Water |
| 1 | 112000 | 97.5 | | 2.5 |
| 4 | 111920 | 99.927 | | 0.073 |
| 3 | 80 | trace | | 100 |
| 6 | 1070 | trace | 62 | 38 |
| 11 | 1150 | trace | 60 | 40 |
| 12 | 111840 | 100 | trace | trace |
| 14 | 133 | trace | 60 | 40 |
| 15 | 53 | | | 100 |

The required refrigeration is provided in conventional manner and the dehydrated hydrocarbon recovered in pipeline 12 at −50° C. and free from ice and hydrate formation at that temperature, is let down to about atmospheric pressure and passed to a cargo space of the tanker ship.

The apparatus may be on the ship itself or on shore or on a floating platform or barge or a tower loading buoy.

EXAMPLE 2

5000 lb/hr of gasoline at a pressure in the range 10 to 20 psig and containing 0.7% by weight of suspended and dissolved water is dehydrated using the process and apparatus described with reference to FIG. 3 of the drawings and employing a methanol/water solution containing approximately 42% methanol by weight and a refrigerator 140 of approximately 5 h.p. (3.73 Kw) capacity. The temperature is coalescer 104 is −25° C. and in separator 106 is −30° C. and the compositions, flow rates and temperatures of the various streams are set out below.

| Pipeline No. | Flow lb/hr | Temp °C. | Composition wt % | | |
|---|---|---|---|---|---|
| | | | Gasoline | Methanol | Water |
| 118 | 5000 | 21 | 99.3 | — | 0.7 |
| 138 | 23.3 | 21 | — | 100.0 | — |
| 142 | 712.3 | 15 | .03 | 41.96 | 58.01 |
| 130 | 747.1 | −30 | .03 | 39.99 | 59.98 |
| 132 | 58.2 | 15 | .03 | 39.99 | 59.98 |

The treated gasoline recovered in pipeline 128 contains less than 0.05% by weight of water and is such that its tendency to form two phases when extended with dry methanol is sufficiently reduced that for most normal purposes and conditions up to 25% by weight of dried methanol may be added.

The apparatus for the process is suitable for installation at a roadside gasoline station to treat gasoline from the storage tanks of the station.

We claim:

1. In a method of removing water dissolved or dispersed in a hydrocarbon feedstock by intimately mixing said hydrocarbon feedstock with a polar organic solvent which is very soluble in water, cooling the mixture whereby the water dissolved or dispersed in said hydrocarbon feedstock is absorbed preferentially in said solvent and a hydrocarbon phase and a solvent-containing aqueous phase are formed, and separating said phases, the improvement in which the hydrocarbon feedstock is selected from light hydrocarbons and mixtures of light hydrocarbons, said hydrocarbon feedstock is mixed in the liquid state with the solvent and the solvent comprises methanol which is employed in the form of an aqueous solution thereof having a methanol concentration no greater than 60% by weight and which solution is substantially insoluble in said hydrocarbon feedstock and has freezing point below the temperature to which the mixture is cooled, said solvent being employed in an amount such that the water content of the aqueous phase after cooling does not exceed that of said solvent by more than 20% by weight, said cooling of said mixture is to a temperature of −20° C. to −60° C., and at least a part of the aqueous phase separated from the hydrocarbon phase after cooling is recycled to provide the aqueous solution to be mixed with fresh hydrocarbon feedstock, and the volume and methanol concentration of the liquor being recycled are each continuously or intermittently restored toward that of the aqueous solution initially employed without distillation by withdrawing a portion of said liquor as a bleedstream and by adding methanol to said recycling stream.

2. A method as claimed in claim 1 in which the hydrocarbon feedstock is selected from liquefied petroleum gas and natural gas liquids.

3. A method as claimed in claim 1 in which the hydrocarbon feedstock is gasoline or aviation turbine fuel.

4. A method as claimed in claim 1 in which the hydrocarbon feedstock is gasoline which is thereafter extended with dried methanol.

5. A method as claimed in claim 1 in which the aqueous methanol solution freezes at a temperature at least 5° C. below the temperature to which the mixture is cooled.

6. A method as claimed in claim 1 in which the concentration of water in the aqueous phase obtained after cooling is not more than 5% greater than that of the water in the aqueous solution.

7. A method as claimed in claim 1 in which the methanol concentration in the aqueous solution is 20 to 60% by weight.

8. A method as claimed in claim 1 in which the amount of aqueous solution mixed with the hydrocarbon feedstock is 5 to 50% by weight of the hydrocarbon feedstock.

9. A method as claimed in claim 1 in which the hydrocarbon feedstock is at a superatmospheric pressure.

10. A method of producing olefinic gases from a hydrocarbon feedstock selected from liquid light hydrocarbons and liquid light hydrocarbon mixtures at a location which is geographically remote from the point of supply of said hydrocarbon feedstock, the method comprising steam cracking at said location said hydrocarbon feedstock which has been transferred thereto from said point of supply at least in part by transportation at subambient temperature in a tanker ship, said hydrocarbon feedstock having been simultaneously treated to remove water therefrom and cooled to a sub-ambient temperature suitable for the storage and transportation of said hydrocarbon feedstock in said tanker ship by the method claimed in claim 21 prior to loading said hydrocarbon feedstock into a cargo space of said tanker ship.

11. A method as claimed in claim 10 in which the hydrocarbon feedstock comprises a condensate the major proportion of which consists of at least one of $C_2$-$C_4$ hydrocarbons and obtained by chilling at superatmospheric pressure a source selected from natural gas and associated gas.

12. A method as claimed in claim 1 in which said mixture is cooled to a sub-ambient temperature and the hydrocarbon phase thereafter separated from the aqueous phase is loaded into the cargo space of a tanker ship for transport therein at said sub-ambient temperature.

13. A method as claimed in claim 12 further comprising discharging said hydrocarbon phase from the cargo space of the tanker ship.

14. A method comprising discharging from the cargo space of a tanker ship, the hydrocarbon phase obtained by the method of claim 1, which hydrocarbon phase has been carried at least in part at sub-ambient temperature in the cargo space of the tanker ship.

15. A method as claimed in claim 1 wherein said hydrocarbon feedstock comprises a hydrocarbon or a mixture of hydrocarbons having a boiling range not substantially exceeding that of aviation turbine fuel.

16. In a method of dispensing gasoline from a storage tank into a fuel tank of a motor vehicle, the improvement comprising removing water from the gasoline by intimately mixing said gasoline in the liquid state with a polar organic solvent which is very soluble in water, cooling the mixture to a temperature of −20° C. to −60° C. whereby water dissolved or dispersed in said gasoline is absorbed preferentially in said solvent and a gasoline phase and a solvent-containing aqueous phase are formed, separating the phases and charging the separated gasoline phase to said fuel tank, and wherein the solvent comprises methanol which is employed in the form of an aqueous solution thereof, said solution being substantially insoluble in the gasoline, having a methanol concentration no greater than 60% by weight and a freezing point below the temperature to which the mixture is cooled and being used in an amount such that the water content of said solvent-containing aqueous phase does not exceed that of said solution by more than 20 percent by weight, and at least a part of the aqueous phase separated from the gasoline after cooling is recycled to provide the aqueous solution to be mixed with more gasoline, and the volume and methanol concentration of the liquor being recycled are each continuously or intermittently restored toward that of the aqueous solution initially employed by withdrawing a portion of said liquor as a bleedstream and by adding methanol to said recycling stream.

17. In a method of dispensing aviation fuel from a storage tank into a fuel tank of an aircraft, the improvement comprising removing water from the aviation fuel by intimately mixing said aviation fuel in the liquid state with a polar organic solvent which is very soluble in water, cooling the mixture to a temperature of −20° C. to −60° C. whereby water dissolved or dispersed in said aviation fuel is absorbed preferentially in said solvent and an aviation fuel phase and a solvent-containing aqueous phase are formed, separating the phases and charging the separated aviation fuel phase to said fuel tank, and wherein the solvent comprises methanol which is employed in the form of an aqueous solution thereof, said solution being substantially insoluble in the aviation fuel, having a methanol concentration no greater than 60% by weight and a freezing point below the temperature to which the mixture is cooled and being used in an amount such that the water content of said solvent-containing aqueous phase does not exceed that of said solution by more than 20 percent by weight, and at least a part of the aqueous phase separated from the aviation fuel after cooling is recycled to provide the aqueous solution to be mixed with more aviation fuel, and the volume and methanol concentration of the liquor being recycled are each continuously or intermittently restored toward that of the aqueous solution initially employed by withdrawing a portion of said liquor as a bleedstream and by adding methanol to said recycling stream.

18. In a method of loading a liquefied light hydrocarbon into a cargo tank of a tanker ship, the improvement comprising simultaneously removing water from the liquefied light hydrocarbon and cooling it to a sub-ambient temperature at which it is to be loaded into said cargo tank by intimately mixing said liquefied light hydrocarbon with a polar organic solvent which is very soluble in water, cooling the mixture to a temperature of −20° C. to −60° C. whereby water dissolved or dispersed in said liquefied light hydrocarbon is absorbed preferentially in said solvent and a liquefied light hydrocarbon phase and a solvent-containing aqueous phase are formed, separating the phases and charging the cooled and separated liquefied light hydrocarbon phase to said cargo tank, and wherein the solvent comprises methanol which is employed in the form of an aqueous solution thereof, said solution being substantially insoluble in the liquefied light hydrocarbon, having a methanol concentration no greater than 60% by weight and a freezing point below the temperature to which the mixture is cooled and being used in an amount such that the water content of said solvent-containing aqueous phase does not exceed that of said solution by more than 20 percent by weight, and at least a part of the aqueous phase separated from the liquefied light hydrocarbon after cooling is recycled to provide the aqueous solution to be mixed with fresh liquefied light hydrocarbon, and the volume and methanol concentration of the liquor being recycled are each continuously or intermittently restored toward that of the aqueous solution initially employed by withdrawing a portion of said liquor as a bleedstream and by adding methanol to said recycling stream.

* * * * *